United States Patent [19]

Thyes et al.

[11] Patent Number: 4,857,658
[45] Date of Patent: Aug. 15, 1989

[54] PREPARATION OF (Z)-2-(2-ARYLETHENYL)ARYLCARBOXYLIC ACIDS

[75] Inventors: Marco Thyes, Ludwigshafen; Gerd Steiner, Kirchheim, both of Fed. Rep. of Germany

[73] Assignee: BASF Aktiengesellschaft, Ludwigshafen, Fed. Rep. of Germany

[21] Appl. No.: 134,108

[22] Filed: Dec. 17, 1987

[51] Int. Cl.$^4$ .............................................. C07C 63/64
[52] U.S. Cl. ................................................ 562/495
[58] Field of Search ........................................ 562/495

[56] References Cited

U.S. PATENT DOCUMENTS 4,723,028  2/1988  Shudo .................................. 562/495

Primary Examiner—Paul J. Killos
Attorney, Agent, or Firm—Keil & Weinkauf

[57] ABSTRACT (Z)-2-(2-arylethenyl)arylcarboxylic acids of the general formula I

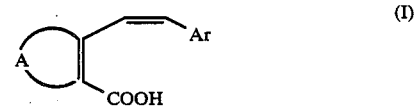

where A is a group for completing an aromatic ring system and Ar is an aromatic radical, are prepared by reacting a 2-formylarylcarboxylic acid of the general formula II

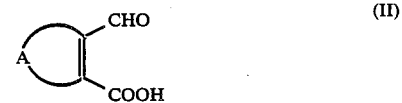

with an (arylmethyl)phosphonium salt of the general formula III

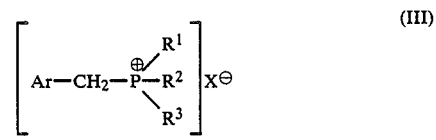

where $R^1$, $R^2$ and $R^3$ are each organic radicals and X is halogen, in the presence of a base at from (−20°) to +30° C. by carrying out the reaction in the presence of a $C_1$–$C_5$-alkanol and/or a $C_2$–$C_4$-alkanediol.

4 Claims, No Drawings

PREPARATION OF (Z)-2-(2-ARYLETHENYL)ARYLCARBOXYLIC ACIDS

The present invention relates to an improved process for preparing a (Z)-2-(2-arylethenyl)arylcarboxylic acid of the general formula I

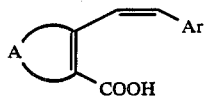   (I)

A is a group for completing an aromatic ring system and Ar is an aromatic radical, by reacting a 2-formylarylcarboxylic acid of the general formula II

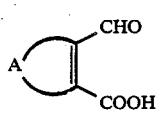   (II)

with an (arylmethyl)phosphonium salt of the general formula III

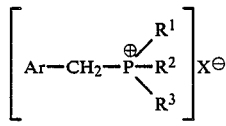   (III)

where $R^1$, $R^2$ and $R^3$ are each organic radicals and X is halogen, in the presence of a base at from $-20°$ C. to $30°$ C., wherein the reaction medium used is a $C_1$-$C_5$-alkanol or a $C_2$-$C_4$-alkanediol.

German Laid-Open Application DOS No. 1,618,706 discloses reacting trifluoromethyl-substituted phthalaldehydic acids with benzyltriphenylphosphonium chloride in tetrahydrofuran at room temperature ($20°$ to $25°$ C.) to give the corresponding 2-(2-arylethenyl)benzoic acid derivatives I' and converting these compounds into the 7-ring ketones IV'

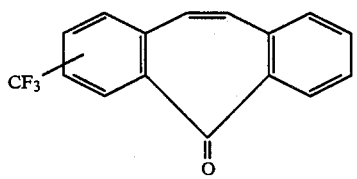   (IV')

Since, however, this Wittig reaction predominantly gives rise to the E-isomers, which on steric grounds are unsuitable from the outset for the cyclization to 7-ring ketones, the compounds I' had to be hydrogenated to the compounds I".

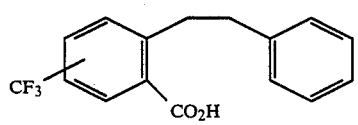   (I")

before the ring closure and dehydrogenated to the compounds IV' after the ring closure.

Similarly, the process of Ind. J. Chem. 22B (1983), produces almost exclusively the E-isomer.

It is an object of the present invention to make the 7-ring ketones IV

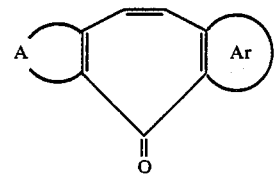   (IV)

accessible in a simpler manner; specifically to design the Wittig reaction in such a way as to produce predominantly the Z-isomer I from which, by cyclization, the compound IV directly obtainable.

We have found that this object is achieved in a process for preparing a (Z)-2-(2-arylethenyl)arylcarboxylic acid of the general formula I

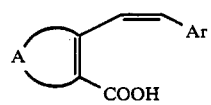   (I)

where A is a group for completing an aromatic ring system and Ar is an aromatic radical, by reacting a 2-formylarylcarboxylic acid of the general formula II

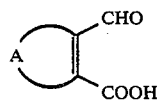   (II)

with an (arylmethyl)phosphonium salt of the general formula III

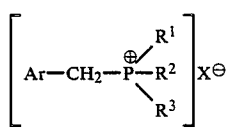   (III)

where $R^1$, $R^2$ and $R^3$ are each organic radicals and X is halogen, in the presence of a base at from ($-20°$) to $30°$ C., which comprises carrying out the reaction in the presence of a $C_1$-$C_5$-alkanol and/or a $C_2$-$C_4$-alkanediol.

Suitable $C_1$-$C_5$-alkanols are methanol, ethanol, n-propanol, isopropanol, n-butanol, iso-butanol, sec-butanol, tert-butanol, the pentanols such as n-pentanol or mixtures thereof, suitable $C_2$-$C_4$-alkanediols are for example ethylene glycol and propane-1,2-diol. The particularly preferred reaction medium is methanol.

The amount of $C_1$-$C_5$-alkanol ranges preferably from 0.8 to 50 ml/g of II, particularly from 1 to 10 ml/g of II. The corresponding preference ranges if a $C_2$-$C_4$-alkanediol is used extend from 1.5 to 60 ml/g of II and from 1.5 to 15 ml/g of II respectively. If a mixture of an alkanol and an alkanediol is used, corresponding average values apply.

In addition to the $C_1$-$C_5$-alkanol and/or the $C_2$-$C_4$-alkanediol it is possible to use further inert solvents, for example aromatic hydrocarbons such as benzene, toluene, ortho-xylene, meta-xylene, para-xylene or a mixture of xylene isomers, or dialkylformamides such as dimethylformamide, diethylformamide or diisoprpylformamide. Preference is given to toluene and dimethylformamide. The mixing ratio of additional solvent, $C_1$–$C_5$-alkanol and/or $C_2$–$C_4$-alkanediol ranges from 0.001:1 to 50:1. preferably from 0.01:1 to 20:1, particularly from 0.01:1 to 5:1.

Preference is given to using a $C_1$–$C_5$-alkanol, in particular methanol, ethanol or tert-butanol, as sole solvent.

The (arylmethyl)phosphonium salt III required for carrying out the process according to the invention is either known or preparable by a known method (Houben-Weyl, Methoden der Organischen Chemie, vol. 12/1, p. 79 et sec.). Similarly, compounds II are either known or preparable by a known method.

Suitable radicals $R^1$ to $R^3$ in the phosphonium cation

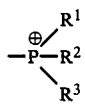

are those which do not react with the phosphonium salt, such as aryl, e.g. phenyl, substituted phenyl, e.g. tolyl, xylyl, mesityl or methoxyphenyl, or even polynuclear radicals, e.g. naphthyl, anthryl or phenanthryl. Preferably, the radicals $R^1$ to $R^3$ are each phenyl. Suitable counterions $X^\ominus$ are halogens, preferably chlorine and bromine.

The reaction is carried out at from ($-20°$) to $+30°$ C., preferably at from ($-10°$) to $+10°$ C.; and in general it is advisable to employ atmospheric pressure.

The structural moiety

in the compounds I and II conforms preferably to benzene. 1,2-naphthalene, 2,3-naphthalene or the halogen, $C_1$–$C_4$-alkyl, $C_1$–$C_4$-alkoxy or trihaloalkyl derivatives thereof.

Ar is for example an unsubstituted aromatic, such as phenyl, 1-naphthyl,-2-naphthyl or anthryl, in particular phenyl, halogen-substituted phenyl, such as monohalophenyl, dihalophenyl or trihalophenyl, in particular monohalophenyl, e.g. 2-, 3- or 4-fluorophenyl, 2-, 3- or 4-chlorophenyl, 2-, 3- or 4-bromophenyl or 4-iodophenyl, or dihalophenyl, e.g. 2,3-, 2,4-, 2,5-, 3,4- or 3,5-difluorophenyl, 2,3-, 2,4-, 2,5-, 3,4- or 3,5-dichlorophenyl, 2,3-, 2,4-, 2,5-, 3,4- or 3,5-dibromophenyl, 2-chloro-4-fluorophenyl, 3-bromo-5-chlorophenyl or 2-fluoro-4-bromophenyl, $C_1$–$C_4$-alkyl-substituted phenyl, such as mono-$C_1$–$C_4$-alkylphenyl, di-$C_1$–$C_4$-alkylphenyl or tri-$C_1$–$C_4$-alkylphenyl in particular mono-$C_1$–$C_4$-alkylphenyl, e.g. 2-, 3- or 4-methylphenyl, 2-, 3- or 4-ethylphenyl, 2-, 3- or 4-n-propylphenyl, 2-, 3- or 4-isopropylphenyl, 2-, 3- or 4-n-butylphenyl, 2-, 3- or 4-isobutylphenyl, 2-, 3- or 4-secbutylphenyl, or 2-, 3- or 4-tert-butylphenyl, or di-$C_1$–$C_4$-alkylphenyl, e.g. 2,3-, 2,4- 2,5-, 3,4- or 3,5-dimethylphenyl, 2,3-, 2,4-, 2,5-, 3,4- or 3,5-diethylphenyl, 2,3-, 2,4-, 2,5-, 3,4- or 3,5-di-n-propylphenyl, 2,3-, 2,4-, 2,5-, 3,4- or 3,5-di-isopropylphenyl, 2,3-, 2,4-, 2,5-, 3,4- or 3,5-di-n-butylphenyl, 2,3-, 2,4-, 2,5-, 3,4- or 3,5-di-isobutylphenyl, 2,3-, 2,4-, 2,5-, 3,4- or 3,5-di-sec-butylphenyl, 2,3-, 2,4-, 2,5-, 3,4- or 3,5-di-tert-butylphenyl, 2-methyl-4-tert-butylphenyl, 3-methyl-5-ethylphenyl or 3-ethyl-4-n-propylphenyl, $C_1$–$C_4$-alkoxy-substituted phenyl, such as mono-$C_1$–$C_4$-alxoyphenyl, di-$C_1$–$C_4$-alkoxyphenyl or tri-$C_1$–$C_4$-alkoxyphenyl, in particular mono-C1-C4-alkoxyphenyl, e.g. 2-, 3- or 4-methoxyphenyl, 2-, 3- or 4-ethoxyphenyl, 2-, 3- or 4-n-propoxyphenyl, 2-, 3- or 4-iso-propoxyphenyl, 2-, 3- or 4-n-butoxyphenyl, 2-, 3- or 4-isobutoxyphenyl, 2-, 3- or 4-sec-butoxyphenyl, 2-, 3- or 4-tert-butoxyphenyl, or di-$C_1$–$C_4$-alkoxyphenyl, e.g. 2,3-, 2,4-, 2,5-, 3,4- or 3,5-dimethoxyphenyl, 2,3-, 2,4-, 2,5-, 3,4- or 3,5-diethoxyphenyl, 2,3-, 2,4-, 2,5-, 3,4- or 3,5-di-n-propoxyphenyl, 2,3-, 2,4-, 2,5-, 3,4- or 3,5-di-iso-propoxyphenyl, 2,3-, 2,4-, 2,5-, 3,4- or 3,5-di-n-butoxyphenyl, 2,3-, 2,4-, 2,5-, 3,4- or 3,5-di-isobutoxyphenyl, 2,3-, 2,4-, 2,5-, 3,4- or 3,5-di-sec-butoxyphenyl, 2,3-, 2,4-, 2,5-, 3,4- or 3,5-di-tert-butoxyphenyl, 2-methoxy-4-tert-butoxyphenyl or 3-ethoxy-5-n-propoxyphenyl, trihalomethyl-substituted phenyl, such as mono-, di- or trihalomethylphenyl, in particular monotrichloromethylphenyl, e.g. 2-, 3- or 4-trichloromethylphenyl, monotrifluoromethylphenyl, e.g. 2-, 3- or 4-trifluoromethylphenyl, ditrichloromethylphenyl, e.g. 2,3-, 2,4-, 2,5-, 3,4- or 3,5-di-trichloromethylphenyl or di-trifluoromethylphenyl, e.g. 2.3-, 2,4-, 2,5-, 3,4- or 3,5-di-trifluoromethylphenyl, cyano-substituted phenyl, such as monocyanophenyl, dicyanophenyl, tricyanophenyl, in particular monocyanophenyl, e.g. 2-cyanophenyl, 3-cyanophenyl or 4-cyanophenyl, or dicyanophenyl, e.g. 2,3-dicyanophenyl, 2,4-dicyanophenyl, 2,5-dicyanophenyl, 3,4-dicyanophenyl or 3,5-dicyanophenyl, nitro-substituted phenyl, such as mononitrophenyl, dinitrophenyl, in particular mononitrophenyl, e.g. 2-nitrophenyl, 3-nitrophenyl or 4-nitrophenyl, $C_1$–$C_4$-alkylmercapto-substituted phenyl, such as mono-$C_1$–$C_4$-alkylmercaptophenyl, di-$C_1$–$C_4$-alkylmercaptophenyl, tri-$C_1$–$C_4$-alkylmercaptophenyl, in particular mono-$C_1$–$C_4$-alkylmercaptophenyl, e.g. 2-, 3- or 4-methylmercaptophenyl, 2-, 3- or 4-ethylmercaptophenyl, 2-, 3- or 4-n-propylmercaptophenyl, 2-, 3- or 4-isopropylmercaptophenyl or 2-, 3- or 4-n-butylmercaptophenyl.

Particular preference is given to those radicals Ar where one ortho position relative to the ethenyl group is occupied by hydrogen.

To prepare a (Z)-2-(2-arylethenyl)arylcarboxylic acid I, the (arylmethyl)phosphonium salt III used can be prepared in situ or be used after isolation. The conversion to a compound I is effected by reacting a 2-formylarylcarboxylic acid II with a compound III in the presence of a preferably not less than equimolar amount of III and in the presence of a base. Particular preference is given to using equimolar amounts of compounds II and III. Advantageously, the arylmethylphosphonium salt III should be introduced initially and the base be added at the end. For every mole of II not less than 2 moles of a base are used The preferred range is from 2.1 to 2.5 moles of base per mole of II.

The base used can be an alkali metal or alkaline earth metal salt of a $C_1$–$C_5$-alkanol or $C_2$–$C_4$-alkanediol or an alkali metal or alkaline earth metal carbonate, particular preference being given to sodium methylate and alkali metal carbonates.

As is known from Agric.Biol.Chem. 45 (1981), 1669, some compounds I are recommended for use as plant growth regulators. Furthermore, the Z-isomers can be used in an isolated form or in the form of an E/Z-isomer mixture to prepare tricyclic ketones which can be converted into pharmacologically active tricyclic compounds (German Laid-Open Application DOS No. 3,009,034).

Of the compounds I which are obtainable by this process, preference is given to the following Z-isomers:
2-(2-phenylethenyl)benzoic acid
2-[2-(2-chlorophenyl)ethenyl]benzoic acid
2-[2-(3-chlorophenyl)ethenyl]benzoic acid
2-[2-(4-chlorophenyl)ethenyl]benzoic acid
2-[2-(3,4-dichlorophenyl)ethenyl]benzoic acid
2-[2-(3-fluorophenyl)ethenyl]benzoic acid
2-[2-(3-trifluoromethyl-phenyl)ethenyl]benzoic acid
2-[2-(3-methoxyphenyl)ethenyl]benzoic acid
2-[2-(2-bromophenyl)ethenyl]benzoic acid
2-[2-(3-bromophenyl)ethenyl]benzoic acid
2-[2-(4-bromophenyl)ethenyl]benzoic acid
2-[2-(2-fluorophenyl)ethenyl]benzoic acid
2-[2-(4-fluorophenyl)ethenyl]benzoic acid
2-[2-(2,3-dichlorophenyl)ethenyl]benzoic acid
2-[2-(2,5-dichlorophenyl)ethenyl]benzoic acid
2-[2-(3,5-dichlorophenyl)ethenyl]benzoic acid
2-[2-(2,3-dibromophenyl)ethenyl]benzoic acid
2-[2-(3,4-dibromophenyl)ethenyl]benzoic acid
2-[2-(2-tolyl)ethenyl]benzoic acid
2-[2-(3-tolyl)ethenyl]benzoic acid
2-[2-(4-tolyl)ethenyl]benzoic acid
2-[2-(2-ethylphenyl)ethenyl]benzoic acid
2-[2-(3-ethylphenyl)ethenyl]benzoic acid
2-[2-(4-ethylphenyl)ethenyl]benzoic acid
2-[2-(3-propylphenyl)ethenyl]benzoic acid
2-[2-(3-isopropylphenyl)ethenyl]benzoic acid
2-[2-(3-butylphenyl)ethenyl]benzoic acid
2-[2-(2,3-dimethylphenyl)ethenyl]benzoic acid
2-[2-(3,4-dimethylphenyl)ethenyl]benzoic acid
2-[2-(3,5-dimethylphenyl)ethenyl]benzoic acid
2-[2-(2-methoxyphenyl)ethenyl]benzoic acid
2-[2-(4-methoxyphenyl)ethenyl]benzoic acid
2-[2-(2-ethoxyphenyl)ethenyl]benzoic acid
2-[2-(3-ethoxyphenyl)ethenyl]benzoic acid
2-[2-(4-ethoxyphenyl)ethenyl]benzoic acid
2-[2-(2,3-dimethoxyphenyl)ethenyl]benzoic acid
2-[2-(3,4-dimethoxyphenyl)ethenyl]benzoic acid
2-[2-(2,5-dimethoxyphenyl)ethenyl]benzoic acid
2-[2-(2-cyanophenyl)ethenyl]benzoic acid
2-[2-(3-cyanophenyl)ethenyl]benzoic acid
2-[2-(4-cyanophenyl)ethenyl]benzoic acid
2-[2-(2-nitrophenyl)ethenyl]benzoic acid
2-[2-(3-nitrophenyl)ethenyl]benzoic acid
2-[2-(4-nitrophenyl)ethenyl]benzoic acid
2-[2-[2-(methylmercapto)phenyl]ethenyl]benzoic acid
2-[2-[3-(methylmercapto)phenyl]ethenyl]benzoic acid
2-[2-[4-(methylmercapto)phenyl]ethenyl]benzoic acid
2-[2-[2-(ethylmercapto)phenyl]ethenyl]benzoic acid
2-[2-[3-(ethylmercapto)phenyl]ethenyl]benzoic acid
2-[2-[4-(ethylmercapto)phenyl]ethenyl]benzoic acid The ratio of the E- and Z-isomer contents in the mix was in each case determinable by $^{13}$C-NMR spectroscopy.

EXAMPLE 1

Preparation of (E/Z)-2-[2-(3-chlorophenyl)ethenyl]benzoic acid

To 260 g (991 mmol) of triphenylphosphine in 150 ml of methanol were added dropwise with stirring 160 g (994 mmol) of 3-chlorobenzyl chloride, and the mixture was heated under reflux for 2 hours. After cooling the reaction mixture down to 0° C., 150 g (999 mmol) of o-phthalaldehydic acid were added with stirring in the course of approximately 1 min. This was followed by the dropwise addition, at 0° C., of 450 g (2.5 mol) of a 30% strength sodium methylate solution in methanol in the course of approximately 45 min. After the dropwise addition was complete, the reaction mixture was stirred at 0° C. for a further 3 h and then poured onto a stirred mixture of 1.5 kg of ice and 3.5 l of water. This was followed by filtration with suction, and the filter residue (triphenylphosphine oxide) was washed with about 700 ml of water. The wash liquor was added to the mother liquor. The combined aqueous phases were extracted with a total of 1 l of methylene chloride, to remove the triphenylphosphine oxide still present therein, and then brought to a strongly acid pH with about 150 ml (ca. 1.87 mol) of concentrated hydrochloric acid. The resulting precipitate was filtered off with suction, thoroughly washed with water and dried in a vacuum drying cabinet to leave 232.3 g (91%) of (E/Z)-2-[2-(3-chlorophenyl)ethenyl]benzoic acid in a ratio of ~23:77 in the form of colorless crystals having a melting point of 118°–121° C.

EXAMPLE 2

Preparation of (E/Z)-2-[2-(3-chlorophenyl)ethenyl]benzoic acid

To 41.2 g (157 mmol) of triphenylphosphine in 25 ml of methanol were added dropwise with stirring 25.2 g (156 mmol) of 3-chlorobenzyl chloride, and the reaction mixture was heated under reflux for 2 hours. After the reaction mixture had been cooled down to room temperature, 23.6 g (157 mmol) of o-phthalaldehydic acid and 47.9 g (347 mmol) of potassium carbonate were added in succession with stirring. The reaction mixture was subsequently stirred at room temperature for 7 days and worked up in a conventional manner to give 32.0 g (79%) of (E/Z)-2-[2-(3-chlorophenyl)ethenyl]benzoic acid in a ratio of ·31:69 in the form of colorless crystals having a melting point of 113°–123° C.

EXAMPLE 3

Preparation of (E/Z)-2-[2-(3-chlorophenyl)ethenyl]benzoic acid

To 105.5 g (249 mmol) of (3-chlorobenzyl)triphenylphosphonium chloride in 200 ml of toluene were added with stirring, at 0° C., 37.5 g (250 mmol) of o-phthalaldehydic acid. At 0°–10° C., 99 g (550 mol) of a 30% strength solution of sodium methylate in methanol were then added dropwise with stirring and stirred in at 0°–10° C. for 3 hours, and the mixture was worked up in a conventional manner to give 62.3 g (97%) of (E/Z)-2-[2-(3-chlorophenyl)ethenyl]benzoic acid in a ratio of ~30:70 in the form of colorless crystals having a melting point of 110°–121° C.

EXAMPLE 4

Preparation of (E/Z)-2 lorophenyl)ethenyl]benzoic acid

To 78 g (297 mmol) of triphenylphosphine in 150 ml of methanol were added dropwise with stirring 48.3 g (300 mmol) of 2-chlorobenzyl chloride, and the reaction mixture was heated under reflux for 2 hours. After the reaction mixture had been cooled down to 0° C., 46.4 g (309 mmol) of o-phthalaldehydic acid were added with stirring in the course of about 1 min. Thereafter 135 g (750 mmol) of a 30% strength solution of sodium methylate in methanol were added at 0°-10° C. with stirring in the course of 45 min and stirred in at 0°-10° C. for 3 hours, and the reaction mixture was worked up in a conventional manner to give 72 g (94%) of (E/Z)-2-[2-(2-chlorophenyl)ethenylbenzoic acid in a ratio of ~11:89 in the form of colorless crystals having a melting point of 144°-148° C.

EXAMPLE 5

Preparation of (E/Z)-2-[2-(4-chlorophenyl)ethenyl]benzoic acid

Example 4 was repeated with 48.3 g (300 mmol) of 4-chlorobenzyl chloride, affording 67.0 g (87%) of (E/Z)-2[2-(4-chlorophenyl)ethenyl]benzoic acid in a ratio of ~32:68 in the form of colorless crystals having a melting point of 127°-131° C.

EXAMPLE 6

Preparation of (E/Z)-2-[2-(3-fluorophenyl)ethenyl]benzoic acid

To 86 g (328 mmol) of triphenylphosphine in 150 ml of methanol were added dropwise with stirring 47.6 g (329 mmol) of 3-fluorobenzyl chloride, and the reaction mixture was heated under reflux for 2 hours. After the reaction mixture had been cooled down to 0° C., 50.5 g (336 mmol) of o-phthalaldehydic acid were added with stirring in the course of about 1 min. Thereafter 149.4 g (830 mmol) of a 30% strength solution of sodium methylate in methanol were added dropwise with stirring at from -5 to 0° C. in the course of 45 min and stirred in at 0° C. for 3 hours, and the reaction mixture was worked up in a conventional manner to give 60.0 g (76%) of (E/Z)-2-[2-(3-fluorophenyl)ethenyl]benzoic acid in a ratio of ~27:73 in the form of colorless crystals having a melting point of 105°-118° C.

Further compounds I where A is in each case —CH=CH—CH=CH— are given in the Table below.

We claim:
1. A process for preparing predominately the isomer (Z)-2-(2-arylethenyl)aryl-carboxylic acid of the formula I

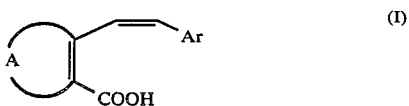

where A is a group for completing an aromatic ring system and Ar is an aromatic radical, which comprises: reacting a 2-formylarylcarboxylic acid of the formula II

with an (arylmethyl)phosphonium salt of the general formula III.

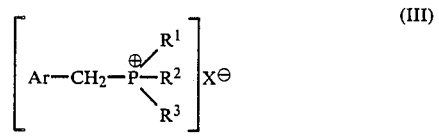

where $R^1$, $R^2$ and $R^3$ are each organic radicals and X is halogen, in the presence of a base at from $(-20°)$ to $+30°$ C. which comprises carrying out the reaction in the presence of a $C_1$-$C_5$-alkanol and/or a $C_2$-$C_4$-alkanediol.

2. The process of claim 1, wherein the 2-formylarylcarboxlic acid II is a phthalaldehydic acid IIa.

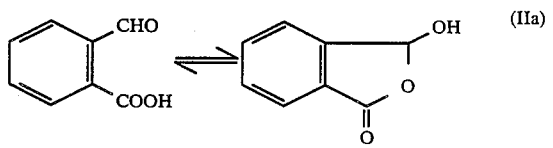

3. The process of claim 1, wherein the (arylmethyl)phosphonium salt III si an (arylmethyl)triphenylphosphonium chloride or bromide.

4. The process of claim 1, wherein from 0.8 to 50 ml of $C_1$-$C_5$-alkanol/g of II and/or from 1.5 to 60 of $C_2$-$C_4$-alkanediol/g of II are used.

| Ar | Base | Prepared acc. to Ex. No. | Reaction temp. [°C.] | Melting point [°C.] | Yield [%] | Z/E ratio |
|---|---|---|---|---|---|---|
| Phenyl | 30% strength NaOCH₃ in CH₃OH | 1 | 0-5 | 120-123 | 77 | ~ 58/42 |
| 3,4-dichlorophenyl | " | 1 | 0 | 151-158 | 84 | ~ 80/20 |
| 3-(Trifluoromethyl)phenyl | " | 1 | (−5)-0 | 127-132 | 79 | ~ 84/16 |
| 3-Methoxyphenyl | " | 1 | 0 | 101-105 | 72 | ~ 61/39 |
| 3-cyanophenyl | " | 1 | 0 | 170-182 | 84 | ~ 87/13 |
| 3-nitrophenyl | " | 1 | 0 | 165-170 | 83 | ~ 86/14 |

UNITED STATES PATENT AND TRADEMARK OFFICE
CERTIFICATE OF CORRECTION

PATENT NO. : 4,857,658
DATED : August 15, 1989
INVENTOR(S) : Marco THYES et al.

It is certified that error appears in the above-identified patent and that said Letters Patent is hereby corrected as shown below:

On the title page Insert

-- Foreign Application Priority Data

Dec. 24, 1986 [DE] Fed. Republic of Germany 3644463 --.

Signed and Sealed this

Nineteenth Day of June, 1990

Attest:

HARRY F. MANBECK, JR.

*Attesting Officer*     *Commissioner of Patents and Trademarks*